United States Patent
Uemura (10) Patent No.: US 10,739,325 B2
(45) Date of Patent: Aug. 11, 2020

(54) AIR-FUEL RATIO SENSOR CONTROL APPARATUS

(71) Applicant: DENSO CORPORATION, Kariya, Aichi-pref. (JP)

(72) Inventor: Shinya Uemura, Kariya (JP)

(73) Assignee: DENSO CORPORATION, Kariya (JP)

( * ) Notice: Subject to any disclaimer, the term of this patent is extended or adjusted under 35 U.S.C. 154(b) by 187 days.

(21) Appl. No.: 15/661,028

(22) Filed: Jul. 27, 2017

(65) Prior Publication Data

US 2018/0128800 A1    May 10, 2018

(30) Foreign Application Priority Data

Nov. 8, 2016   (JP) .................... 2016-218061

(51) Int. Cl.
| | |
|---|---|
| *F02D 41/00* | (2006.01) |
| *G01N 33/00* | (2006.01) |
| *F02D 41/14* | (2006.01) |
| *G01N 27/22* | (2006.01) |
| *G01M 15/10* | (2006.01) |

(52) U.S. Cl.
CPC ..... *G01N 33/0062* (2013.01); *F02D 41/1454* (2013.01); *G01N 27/221* (2013.01); *F02D 2250/14* (2013.01); *G01M 15/102* (2013.01); *G01N 2027/222* (2013.01)

(58) Field of Classification Search
CPC .. F02D 41/1454; F02D 41/28; F02D 41/1455; F02D 2250/14; G01N 27/419; G01N 27/407; G01N 27/4065; G01N 33/0062; G01M 15/104; G01M 15/102
See application file for complete search history.

(56) References Cited

U.S. PATENT DOCUMENTS

| | | | | |
|---|---|---|---|---|
| 5,405,521 A | * | 4/1995 | Nakamori | ........... F02D 41/1455 |
| | | | | 204/406 |
| 2006/0011476 A1 | | 1/2006 | Hada et al. | |
| 2015/0219590 A1 | | 8/2015 | Uemura et al. | |

FOREIGN PATENT DOCUMENTS

JP         2003-329637 A      11/2003

* cited by examiner

*Primary Examiner* — Blake A Tankersley
(74) *Attorney, Agent, or Firm* — Posz Law Group, PLC (57) ABSTRACT

An air-fuel ratio sensor control apparatus comprises a voltage control part configured to control a voltage Vo1 applied to a cell of an air-fuel ratio sensor in accordance with a sensor current flowing in the cell and a current detection part configured to detect the sensor current as a physical value, which indicates the air-fuel ratio. In the air-fuel ratio sensor control apparatus, a voltage varying time point, at which the voltage control part varies the voltage Vo1, and a current detecting time point, at which the current detection part detects the current, are shifted from each other. A time period Ta from the current detecting time point, which is immediately before the voltage varying time point, to the voltage varying time point and a time period Tb from the voltage varying time point to the current detecting time period, which is immediately after the voltage varying time point, are set to satisfy Ta<Tb.

10 Claims, 7 Drawing Sheets

AIR-FUEL RATIO SENSOR CONTROL APPARATUS

CROSS REFERENCE TO RELATED APPLICATION

The present application is based on Japanese patent application No. 2016-218061 flied on Nov. 8, 2016, the whole contents of which are incorporated herein by reference.

FIELD

The present disclosure relates to an air-fuel ratio sensor control apparatus.

BACKGROUND

In a conventional air-fuel ratio sensor control apparatus, a voltage is applied to a cell of an air-fuel ratio sensor and a current flowing in the cell is detected as a sensor current, which indicates an air-fuel ratio. In an air-fuel ratio sensor control apparatus disclosed in JP 2015-148471A (US 2015/0219590 A1), a DC voltage applied to a sensor is varied in accordance with a sensor current.

The cell of the air-fuel ratio sensor has a capacitive component (that is, electrostatic capacitance). For this reason, in case of digitally controlling the voltage applied to the cell, a step change of the voltage causes a current flow in the cell through the capacitive component. In case that the current flowing through the capacitive component of the cell (hereinafter referred to as a capacitive current) is detected as a part of the sensor current, accuracy of air-fuel ratio detection is lowered.

SUMMARY

It is therefore an object of to improve accuracy of air-fuel ratio detection.

According to one aspect, an air-fuel ratio sensor control apparatus comprise a voltage control part configured to control a voltage applied to a cell of an air-fuel ratio sensor in accordance with a predetermined physical value outputted from the air-fuel ratio sensor and a current detection part configured to detect a current flowing in the cell as a physical value, which indicates the air-fuel ratio. The voltage control part and the current detection part are configured to vary the voltage and detect the current at a voltage varying time point and a current detecting time point, respectively, which are shifted from each other.

BRIEF DESCRIPTION OF THE DRAWINGS

FIG. 1 is an operational diagram showing an operation of the air-fuel ratio sensor control apparatus according to the second embodiment;

DETAILED DESCRIPTION OF THE EMBODIMENT

An air-fuel ratio sensor control apparatus will be described below with reference to embodiments shown in the drawings.

1. First Embodiment

[1-1. Configuration]

Figure 1:
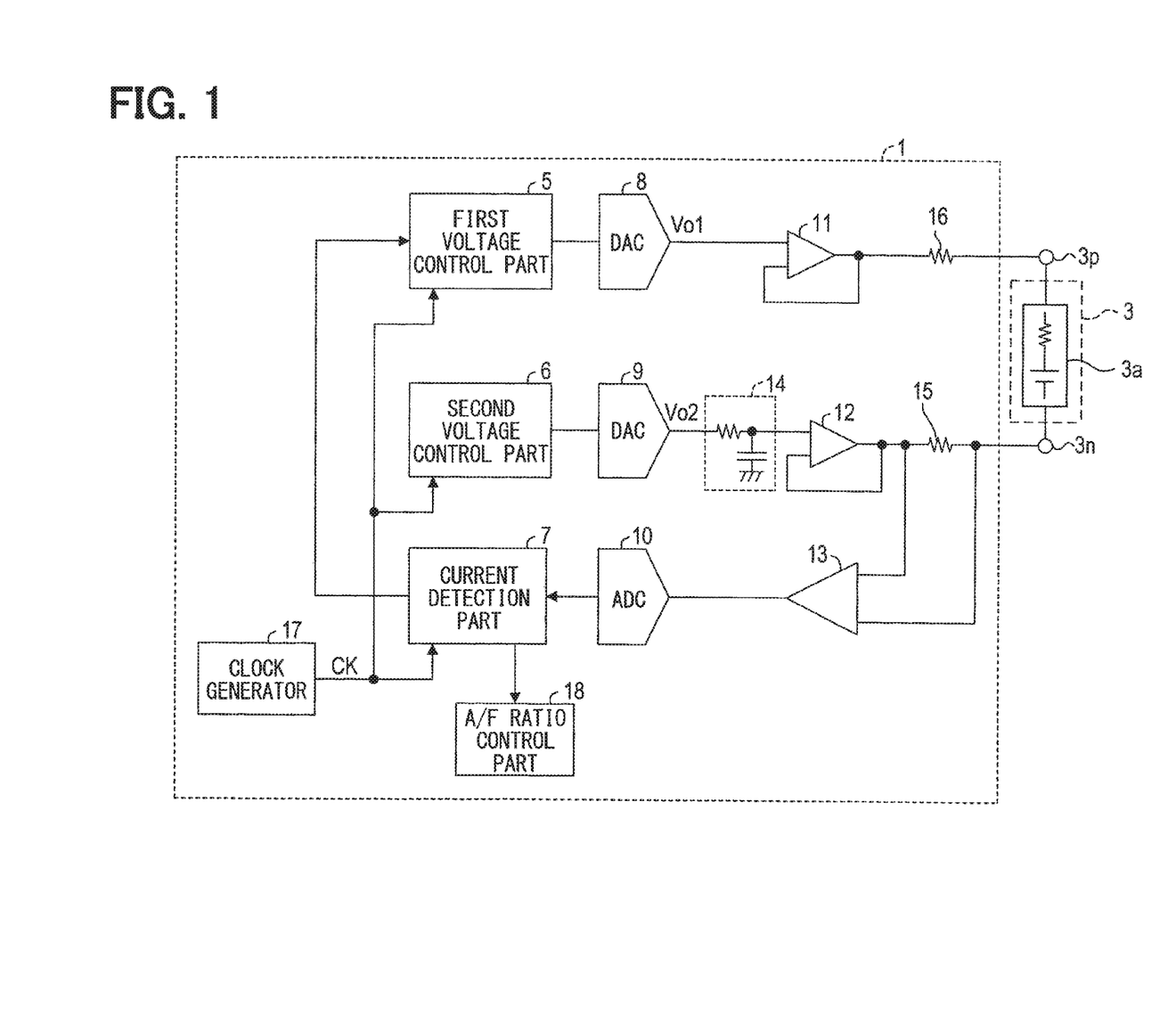
FIG. 1 is a block diagram showing an air-fuel ratio sensor control apparatus according to a first embodiment.

Referring first to FIG. 1, an air-fuel ratio sensor control apparatus, which is an electronic control unit (hereinafter referred to as ECU) 1, is connected to an air-fuel ratio sensor 3, which detects an air-fuel ratio (A/F ratio).

The air-fuel ratio sensor 3 is an air-fuel ratio sensor of a single cell type, which is a limit current type having one cell 3a only. The air-fuel ratio sensor 3 is positioned in an exhaust passage of an engine of a vehicle. The cell 3a of the air-fuel ratio sensor 3 generates a limit current, which varies with an air-fuel ratio in exhaust gas, when a voltage is applied by the ECU 1. The limit current flowing in the cell 3a is a sensor current, which indicates the air-fuel ratio in the exhaust passage detected by the air-fuel ratio sensor 3.

The ECU 1 includes a first voltage control part 5, a second voltage control part 6, a current detection part 7, D/A converters (DACs) 8, 9, an A/D converter (ADC) 10, buffer circuits 11, 12, an amplifier circuit 13, a filter circuit 14, a current detection resistor 15, a protection resistor 16, a clock generator 17 and an air-fuel ratio control part 18.

One end of the current detection resistor 15 is connected to one terminal (for example, negative-side terminal) 3n of the cell 3a. One end of the protection resistor 16 is connected to the other terminal (for example, positive-side terminal) 3p of the cell 3a. The current detection resistor 15 and the protection resistor 16 are simply referred to as resistors, respectively.

The first D/A converter 8 outputs a first voltage Vo1 corresponding to a first digital signal (first command) outputted from the first voltage control part 5. The voltage applied to the air-fuel ratio sensor 3 is a DC voltage. The first voltage Vo1 of the first D/A converter 8 is applied to the buffer circuit 11. The buffer circuit 11 outputs a same voltage as the first voltage Vo1 of the first D/A converter 8 to the other end of the protection resistor 16, which is opposite to the cell 3a side.

The second D/A converter 9 outputs a second voltage Vo2 corresponding to a second digital signal (second command) outputted from the second voltage control part 6. The filter circuit 14 is a low-pass filter circuit, which is formed of a resistor and a capacitor, for example. The second voltage Vo2 of the second D/A converter 9 is applied to the filter circuit 14. An output voltage of the filter circuit 14 is applied to the buffer circuit 12. The buffer circuit 12 outputs a same voltage as the output voltage of the filter circuit 14 to the other end of the resistor 15, which is opposite to the cell 3a side. In the first embodiment, the first voltage Vo1 is set to be larger than the second voltage Vo2 (Vo1>Vo2).

As a result, a differential voltage Vo1−Vo2 is applied to the cell 3a through the resistors 15 and 16 as an application voltage to the cell 3a of the air-fuel ratio sensor 3a for air-fuel ratio detection. A same current as a current (that is, sensor current), which flows in the cell 3a in accordance with the air-fuel ratio, flows in the current detection resistor 15.

The amplifier circuit 13 outputs a voltage by amplifying a potential difference between both ends of the current detection resistor 15. The A/D converter 10 A/D-converts the output voltage of the amplifier circuit 13 in response to the command from the current detection part 7 and outputs a digital signal corresponding to this A/D conversion result to the current detection part 7. In the first embodiment, the digital signal outputted from the A/D converter 10 corresponds to the detection result of the sensor current. A time point, at which the current detection part 7 commands the A/D converter 10 to A/D-convert the output voltage of the amplifier circuit 13, corresponds to a time point for detecting a sensor current (that is, current detecting time point).

The current detection part 7 acquires a digital signal from the A/D converter 10 by operating the A/D converter 10 and calculates the sensor current based on the acquired digital signal. Specifically, the current detection part 7 executes conversion processing for converting an acquired digital signal value to a sensor current value.

The air-fuel ratio control part 18 converts the sensor current calculated by the current detection part 7 into the air-fuel ratio and executes conventional air-fuel ratio feedback control processing, which is processing for correcting a quantity of fuel injection into the engine based on the converted air-fuel ratio.

The clock generator 17 generates and outputs a clock CK of a fixed cycle period, that is, of a fixed frequency. The first voltage control part 5, the second voltage control part 6 and the current detection part 7 operate in synchronization with the clock outputted from the clock generator 17.

The first voltage control part 5 controls the first voltage Vo1 of the first D/A converter 8 in accordance with the sensor current calculated by the current detection part 7. In the first embodiment, the application voltage to the cell 3a is controlled by controlling the first voltage Vo1 of the first D/A converter 8. Specifically, the first voltage control part 5 controls the first voltage Vo1 of the first D/A converter 8 to, for example, an intermediate value in a voltage range, in which the air-fuel ratio and the sensor current uniquely correspond, in accordance with the sensor current. For example, the first voltage Vo1 of the first D/A converter 8 is varied to a larger value as the sensor current increases with an increase in the air-fuel ratio.

In a normal case that processing for detecting an impedance of the cell 3a is not executed by the current detection part 7 and the like, for example, the second voltage control part 6 fixes the second voltage Vo2 of the second D/A converter 9 to a fixed value so that the application voltage varies with the first voltage Vo1.

In case that the processing for detecting the impedance of the cell 3a is executed, the second voltage control part 6 alternately switches over the second voltage Vo2 of the second D/A converter 9 to two kinds of DC voltages of different voltage values at a predetermined switchover period, for example. Even in case that the second voltage Vo2 of the second D/A converter 9 is switched over alternately to two kinds of DC voltages, the voltage outputted to the buffer circuit 12 is filtered by the filter circuit 14 to a smoothed voltage, from which sharp changes are removed, and hence no capacitive current flows in the cell 3a.

The first voltage control part 5, the second voltage control part 6, the current detection part 7 and the air-fuel ratio control part 18 is provided by a microcomputer, which includes a CPU and semiconductor memories (hereinafter referred to as memories) such as a RAM, a ROM and a flash memory. That is, each function of the first voltage control part 5, the second voltage control part 6, the current detection part 7 and the air-fuel ratio control part 18 is realized by the CPU, which executes programs stored in a non-transitory storage medium, which is the memory of the microcomputer. By execution of the programs, methods corresponding to the programs are performed. The first voltage control part 5, the second voltage control part 6, the current detection part 7 and the air-fuel ratio control part 18 may be provided by a single microcomputer or multiple microcomputers. The functions of the first voltage control part 5, the second voltage control part 6, the current detection part 7 and the air-fuel ratio control part 18 may be performed by execution of software by the microcomputer. Alternatively, a part of or all of the functions may be provided by one or multiple hardware. In case that the functions described above are performed by an electronic circuit, which is hardware, the electronic circuit may be configured as a digital circuit including a number of logic circuits, an analog circuit or a combination of the digital circuit and the analog circuit.

[1-2. Operation]

Figure 2:
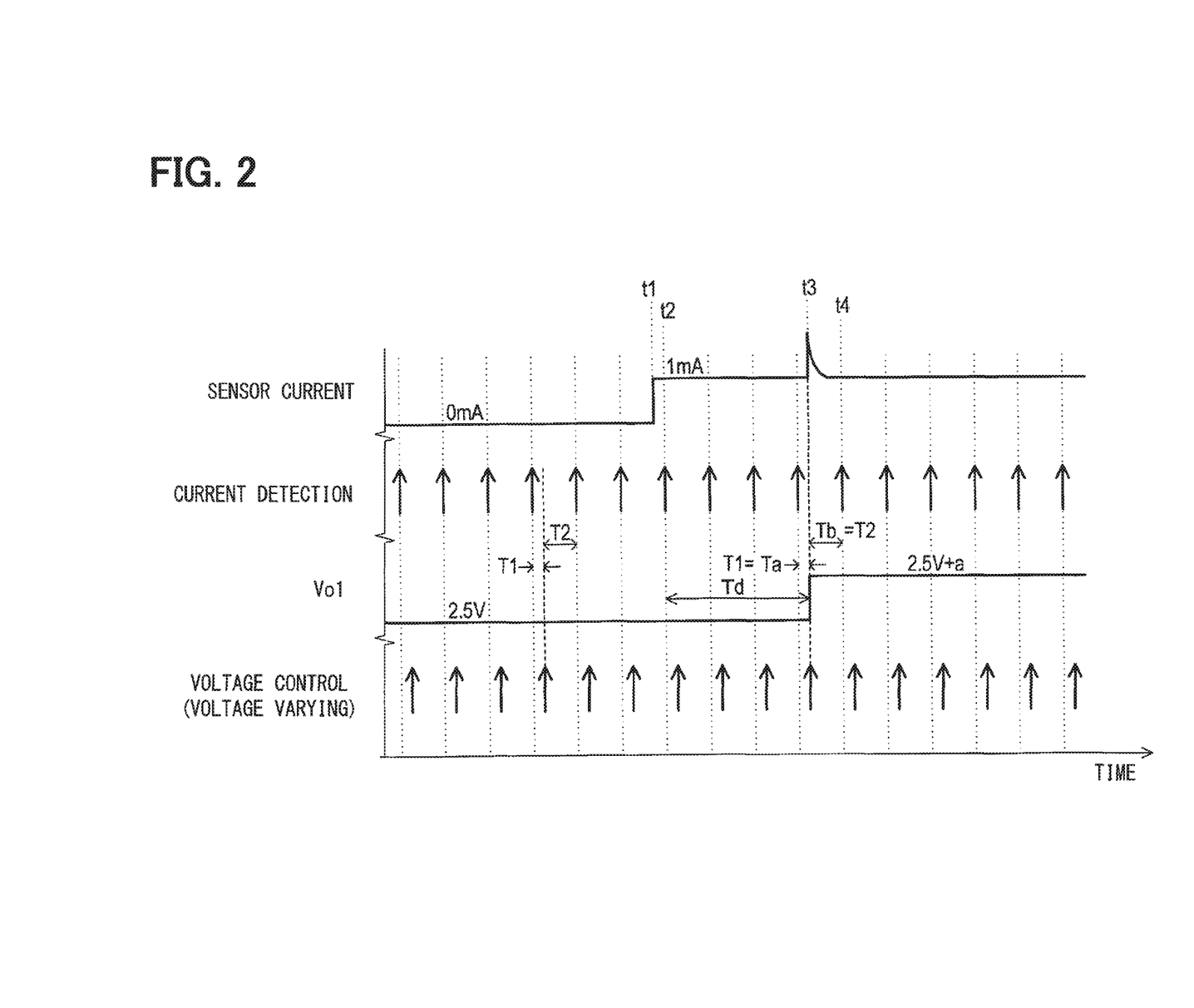
FIG. 2 is an operational diagram showing an operation of the air-fuel ratio sensor control apparatus according to the first embodiment.

In operation of the ECU 1, the current detection part 7 commands the A/D converter 10 to convert the output voltage of the amplifier circuit 13, that is, the current detection part 7 detects the sensor current, at time points (A/D converting time point and current detecting time point) of the fixed cycle period as indicated by an upward-directed arrow in the second stage in FIG. 2.

The first voltage control part 5 controls the first voltage Vo1 of the first D/A converter 8 at time point (voltage control time point), which is between two successive current detecting time points as indicated by an upward-directed arrow in the fourth stage in FIG. 2.

The first voltage control part 5 varies the first voltage Vo1 of the first D/A converter 8 at the voltage control time point by executing processing for varying the first voltage Vo1, that is, processing for varying the first digital signal applied to the first D/A converter 8. As a result, the time point of voltage control is the time point, at which the first voltage control part 5 varies the application voltage to the cell 3a, (that is, voltage varying time point).

That is, according to the ECU 1, the current detecting time point for detecting the sensor current by the current detection part 7 and the voltage varying time point for varying the application voltage to the cell 3a by the first voltage control part 5 in accordance with the sensor current are shifted.

As shown in FIG. 2, a time period T1, which is from the current detecting time point to the next voltage control time point, is set to be shorter than a time period T2, which is from the voltage control time point to the next current detecting time point, that is, T1<T2. Specifically, the time period T1 is shorter than one-half of the cycle period of current detection.

For this reason, when the first voltage Vo1 of the first D/A converter 8 is varied at any one of the voltage control time points, a time period Ta from the current detecting time point, which immediately precedes the voltage varying time point, to the voltage varying time point equals the time period T1. A time period Tb from the voltage varying time point to the current detecting time point, which immediately follows the voltage varying time point, equals the time period T2. As a result, the time period Ta is shorter than the time period Tb. The time period Tb is longer than the time period Ta.

It is assumed in FIG. 2, for example, that the sensor current varies in response to a variation in the air-fuel ratio at time point t1 and the current detection part 7 detects the sensor current after the sensor current variation at time point t2, which is the current detecting time point immediately following the time point U.

In this case, the first voltage control part 5 varies the first voltage Vo1 of the first D/A converter 8 to a value, which corresponds to the varied sensor current detected by the current detection part 7, at any one of the voltage control time points following the time point t2. In this exemplary case, the first voltage control part 5 varies the first voltage Vo1 of the first D/A converter 8 at a voltage control time point t3, which is after an elapse of a predetermined processing time period Td from time point t2. With this variation of the first voltage Vo1, the application voltage to the cell 3a varies stepwisely and the capacitive current flows in the cell 3a. As a result, as shown at time point t3, the capacitive current is included in the sensor current.

In case that the current detection part 7 detects the capacitive current flowing in the cell 3a as a part of the sensor current, the accuracy of air-fuel ratio detection is lowered. According to the ECU 1 described above, the voltage control time point (that is, voltage varying time point) and the current detecting time point are shifted from each other. For this reason, the current detection part 7 detects the sensor current at the current detecting time point after time point t3, at which the application voltage to the cell 3a is varied, that is, at time t4, which is after time point t3 by the time period T2=Tb. At time point t4, the capacitive current is sufficiently reduced and the sensor current is converged to a value, which indicates the actual air-fuel ratio.

[1-3. Advantage]

The first embodiment described above provides following advantages.

(1a) According to the ECU 1, the voltage varying time point of the first voltage control part 5 and the current detecting time point of the current detection part 7 are shifted. That is, the variation of the application voltage in accordance with the sensor current and the detection of the sensor current are performed at different time points.

In case that the application voltage to the cell 3a is varied by the first voltage control part 5, the current detection part 7 detects the current at the time point shifted from the time point of voltage variation. It is thus possible to suppress the capacitive current of the cell 3a from being included in the sensor current, which the current detection part 7 detects. As a result, it is possible to improve the accuracy of detecting the air-fuel ration based on the detected current.

(1b) The current is detected at every fixed time interval and the voltage is varied at the time point, which is between the successive two of the current detecting time points. Further, the time period Ta from the current detecting time point, which is immediately before the voltage varying time point, to the voltage varying time point is set to be shorter than the time period Tb from the voltage varying time point to the current detecting time point, which is immediately after the voltage varying time point.

It is allowable to set that the time period Ta is longer than the time period Tb, that is, Ta>Tb, as opposed to the above-described setting Ta<Tb in the first embodiment. It is however preferred to lengthen the time period Tb, which is from varying the application voltage to the cell 3a to detecting the sensor current, by setting Ta<Tb as set in the first embodiment. It is easier to suppress the possibility that the capacitive current is detected as a part of the sensor current.

(1c) The first voltage control part 5 acquires the sensor current detected by the current detection part 7 as a predetermined physical value outputted from the air-fuel ratio sensor 3 and controls the application voltage to the cell 3a. It is thus possible to use the ECU 1 for single cell type air-fuel ratio sensor.

In the first embodiment, the first voltage control part 5 is a voltage control part and the current flowing in the cell 3a (that is, sensor current) is a physical value of a detection object, which indicates the air-fuel ratio.

2. Second Embodiment

[2-1. Difference from First Embodiment]

A second embodiment is similar to the first embodiment in basic configuration and hence only differences from the first embodiment will be described. The same reference signs indicate the same configuration as the first embodiment.

Figure 3:
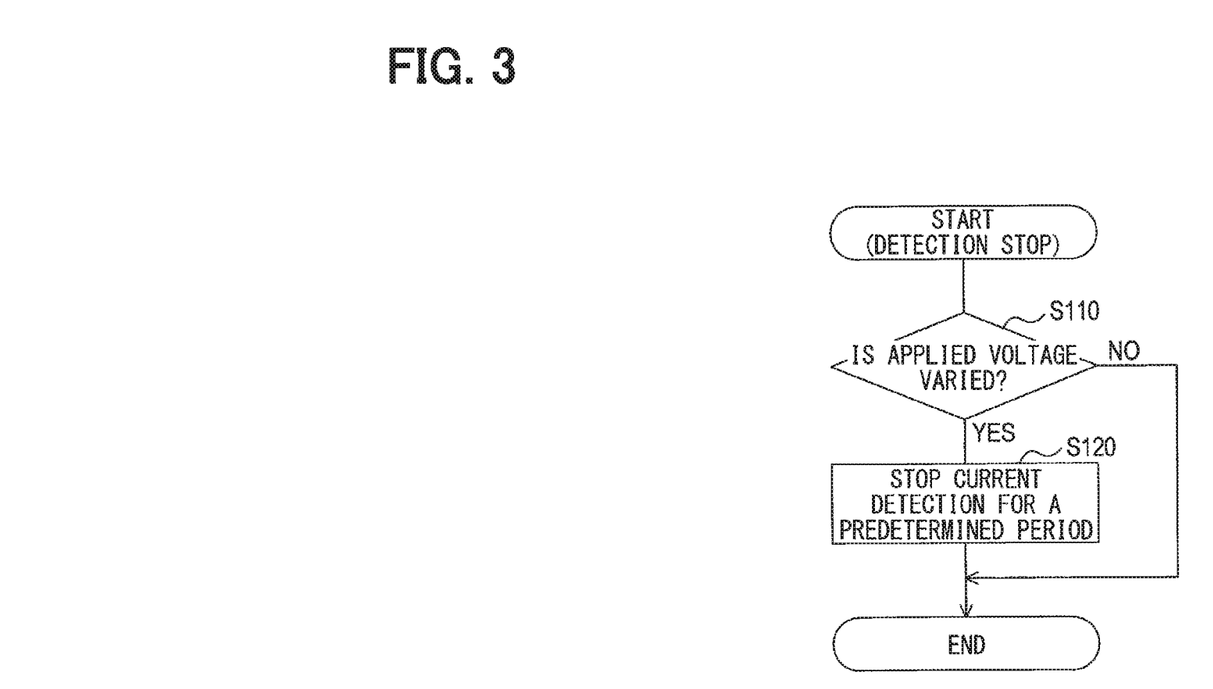
FIG. 3 is a flowchart showing detection stop processing executed by air-fuel ratio sensor control apparatuses according to second and fourth embodiments.

The ECU 1 according to the second embodiment is different from the first embodiment in that the current detection part 7 executes detection stop processing shown in FIG. 3. The current detection part 7 executes the detection stop processing of FIG. 3 at a fixed time interval, which is shorter than the current detection time interval.

As shown in FIG. 3, the current detection part 7 checks whether the application voltage to the cell 3a was varied by the first voltage control part 5 at 5110 after starting the detection stop processing. Specifically, the current detection part 7 checks whether the first voltage Vo1 of the first D/A converter 8 was varied. Whether the first voltage Vo1 was varied may be checked, for example, by monitoring the first digital signal outputted from the first voltage control part 5 to the first D/A converter 8 or by acquiring information, which indicates that the first voltage Vo1 was varied, from the first voltage control part 5. Upon determination that the application voltage to the sell 3a was varied by the first voltage control part 5, the current detection part 7 stops detection of the sensor current for a predetermined time period at 5120. This predetermined time period is set to be more than integer times (N-times) of the time interval of the current detection. N is one preferably larger than two or more.

[2-2. Operation]

Figure 4:
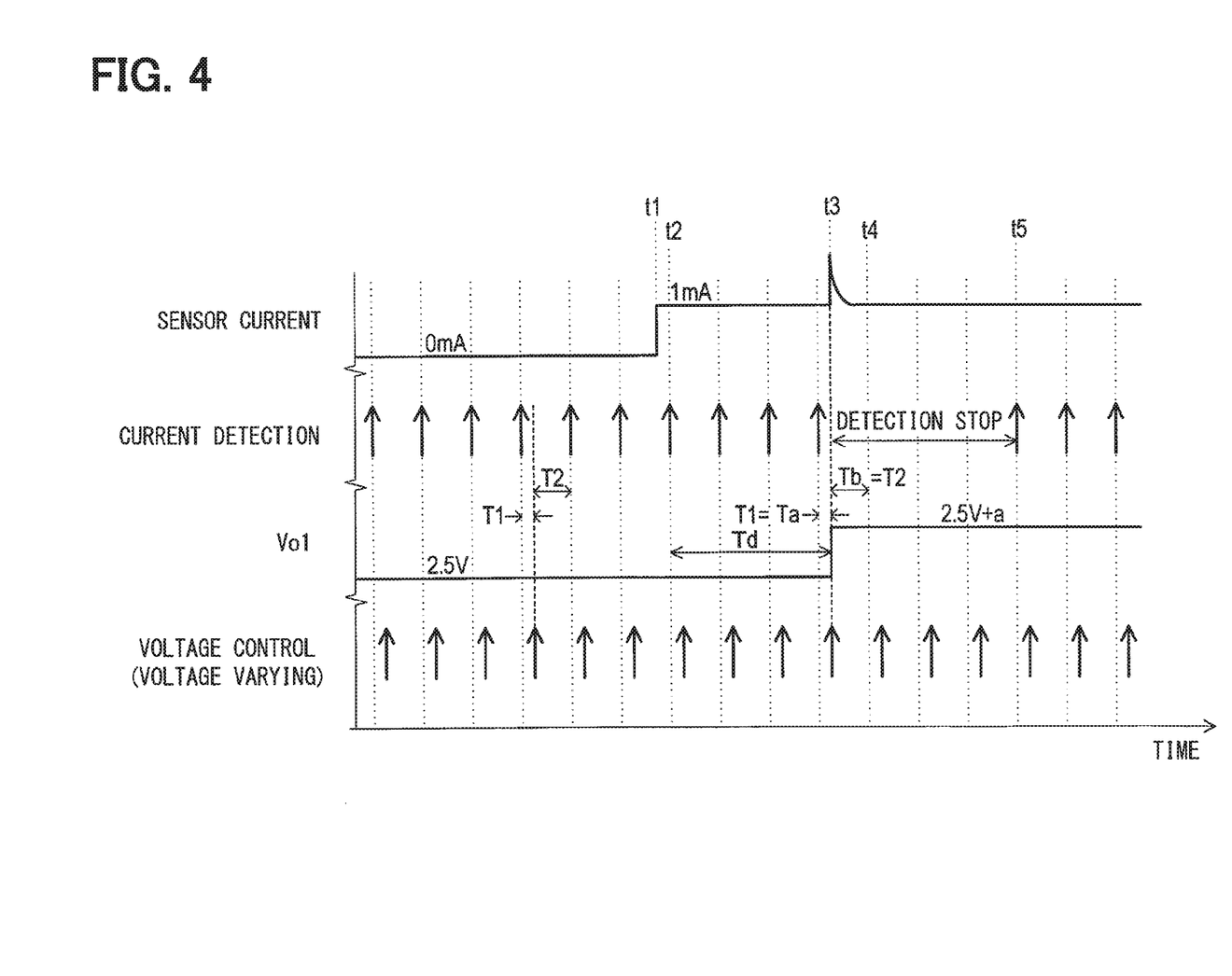

As shown in FIG. 4, which shows a similar example of operation as FIG. 2, when the first voltage control part 5 varies the first voltage Vo1 of the first D/A converter 8 at time point t3, the current detection part 7 stops detecting the sensor current for a predetermined time period. The current detection part 7 starts again detecting the sensor current from time point t5, which is the current detecting time point after an elapse of the predetermined time period. In FIG. 4, the operation from time point t1 to time point t3 is the same as in FIG. 2. In the example shown in FIG. 4, N is assumed to be 3. That is, the current detection part 7 stops detecting the sensor current from time point t3 to a third current detecting time point and detects the sensor current again at time point t5, which is a fourth current detecting time point.

[2-3. Advantage]

The second embodiment provides the following advantage in addition to the similar advantages of the first embodiment. That is, when the first voltage control part 5 varies the application voltage to the cell 3a, the current detection part 7 stops the sensor current detection for the predetermined period. It is thus possible to more surely suppress the capacitive current, which flows in response to the variation of the applied voltage, from being detected as a part of the sensor current.

3. Third Embodiment

[3-1. Configuration]

Figure 5:
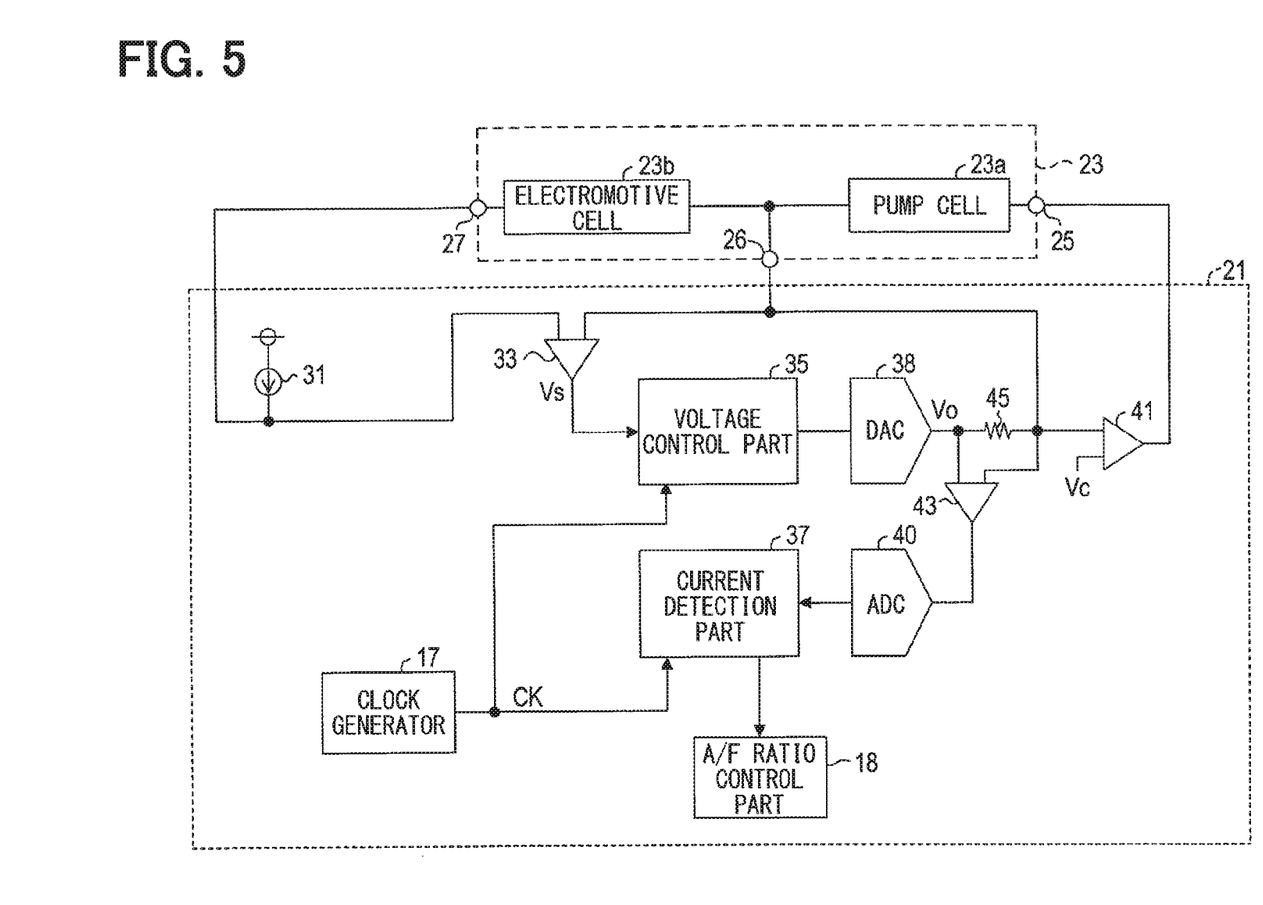
FIG. 5 is a block diagram showing an air-fuel ratio sensor control apparatus according to a third embodiment.

As shown in FIG. 5, an ECU 21 according to a third embodiment is connected to a two-cell type air-fuel ratio sensor 23, which includes a pump cell 23a and an electromotive cell 23b. The air-fuel ratio sensor 23 has a diffusion chamber, into which exhaust gas is introduced, and a reference oxygen chamber. The pump chamber 23a is driven so that an output voltage (that is, electromotive force), which is generated by the electromotive cell 23b in accordance with a difference between oxygen concentrations in the diffusion chamber and the reference oxygen chamber, attains a target value. A sensor current, which flows in the pump cell 23, indicates the air-fuel ratio. In this example, the air-fuel ratio sensor 23 has terminals 25 to 27. The terminal 25 is a positive-side terminal of the pump cell 23a. The terminal 26 is a negative-side terminal, which is common to both of the pump cell 23a and the electromotive cell 23b. The terminal 27 is a positive-side terminal of the electromotive cell 23b.

The ECU 21 includes a constant current circuit 31, an amplifier 33, a voltage control part 35, a current detection part 37, a D/A converter 38, an A/D converter 40, an operational amplifier 41, an amplifier 43 and a current detection resistor 45. Similarly to the ECU 1, the ECU 21 also includes the clock generator 17 and the air-fuel ratio control part 18.

The constant current circuit 31 applies a constant current to the terminal of the air-fuel ratio sensor 23 so that the electromotive cell 23b generates the electromotive force. The amplifier 33 amplifies a voltage developed between the terminals 26 and 27 of the air-fuel ratio sensor 23, that is, an output voltage Vs of the electromotive cell 23b, and outputs the amplified voltage. A gain of the amplifier 33 is assumed to be 1 for simplicity of description. That is, the amplifier 33 is assumed to output the same voltage as the output voltage Vs of the electromotive cell 23b.

The D/A converter 38 outputs a voltage commanded by the voltage control part 35 as a digital signal (command). An output terminal of the D/A converter 38 is connected to the terminal 26 of the air-fuel ratio sensor 23 through the resistor 45.

The operational amplifier 41 receives a voltage of the terminal 26 and a constant voltage Vc (for example, 2.5V). An output terminal of the operational amplifier 41 is connected to the terminal 25 of the air-fuel ratio sensor 23. The operational amplifier 41 regulates the voltage of the terminal so that the voltage of the terminal 26 equals the constant voltage Vc.

A same current as the current flowing in the pump cell 23a flows to the resistor 45. The amplifier 43 amplifies a difference of potentials between both ends of the resistor 45 and outputs an amplified voltage. The A/D converter 40 A/D-converts the output voltage of the amplifier 43 in response to a command from the current detection part 37 and outputs a digital signal indicating an A/D conversion result to the current detection part 37.

The output voltage Vs of the electromotive cell 23b is applied to the voltage control part 35 through the amplifier 33. The voltage control part 35 operates in synchronization with the clock CK applied from the clock generator 17. The voltage control part 35 acquires the output voltage Vs of the electromotive cell 23b at a fixed time interval and controls an output voltage Vo of the D/A converter 38 so that the output voltage Vs attains a target value, which is the constant voltage. When the output voltage Vo of the D/A converter 38 varies, the output voltage of the operational amplifier 41 varies. As a result, the voltage applied to the pump cell 23a varies and the current flowing in the pump cell 23a varies. That is, the voltage applied to the pump cell 23a is controlled by controlling the output voltage Vo of the D/A converter 38.

The current detection part 37 also operates in synchronization with the clock CK outputted from the clock generator 17. The current detection part 37 commands the A/D converter 40 to operate, acquires the digital signal from the A/D converter 40 and calculates the current flowing in the pump cell 23a based on the acquired digital signal. Specifically, the current detection part 37 executes conversion processing from an acquired digital signal value to a current value. In the third embodiment, the current flowing in the pump cell 23a is a physical value of a detection object, which indicates the air-fuel ratio. For this reason, the current flowing in the pump cell 23a is the sensor current. The digital signal outputted from the A/D converter 40 is the detection result of the sensor current. The time point, at which the current detection part 37 causes the A/D converter 40 to A/D-convert the output voltage of the amplifier 43, is the time point for detecting the sensor current (that is, current detecting time point).

The air-fuel ratio control part 18 converts the sensor current calculated by the current detection part 7 into the air-fuel ratio and executes the conventional air-fuel ratio feedback control processing, which is processing for correcting a quantity of fuel injection into the engine based on the converted air-fuel ratio.

That is, in the ECU 21, the voltage control part 35 controls the application voltage to the pump cell 23a so that the output voltage Vs of the electromotive cell 23b attains the constant voltage and the sensor current flows in the pump cell 23a and the resistor 45 in accordance with the air-fuel ratio. Thus the current detection part 37 detects the sensor current by A/D-converting the output voltage of the amplifier 43 by using the A/D converter 40 and the air-fuel ratio control part 18 detects the air-fuel ratio from the sensor current detected by the current detection part 37.

In the ECU 21 as well, the voltage control part 35, the current detection part 37 and the air-fuel ratio control part 18 are provided by a microcomputer, which includes a CPU and memories. That is, each function of the voltage control part 35, the current detection part 37 and the air-fuel ratio control part 18 is realized by the CPU, which executes programs stored in a non-transitory storage medium, which is the memory of the microcomputer. By execution of the programs, methods corresponding to the programs are performed. The voltage control part 35, the current detection part 37 and the air-fuel ratio control part 18 may be provided by a single microcomputer or multiple microcomputers. The functions of the voltage control part 35, the current detection part 37 and the air-fuel ratio control part 18 may be performed by execution of software. Alternatively, a part of or all of the functions may be provided by one or multiple hardware. In case that the functions described above are performed by an electronic circuit, which is hardware, the electronic circuit may be configured as a digital circuit including a number of logic circuits, an analog circuit or a combination of the digital circuit and the analog circuit.

[3-2. Operation]

Figure 6:
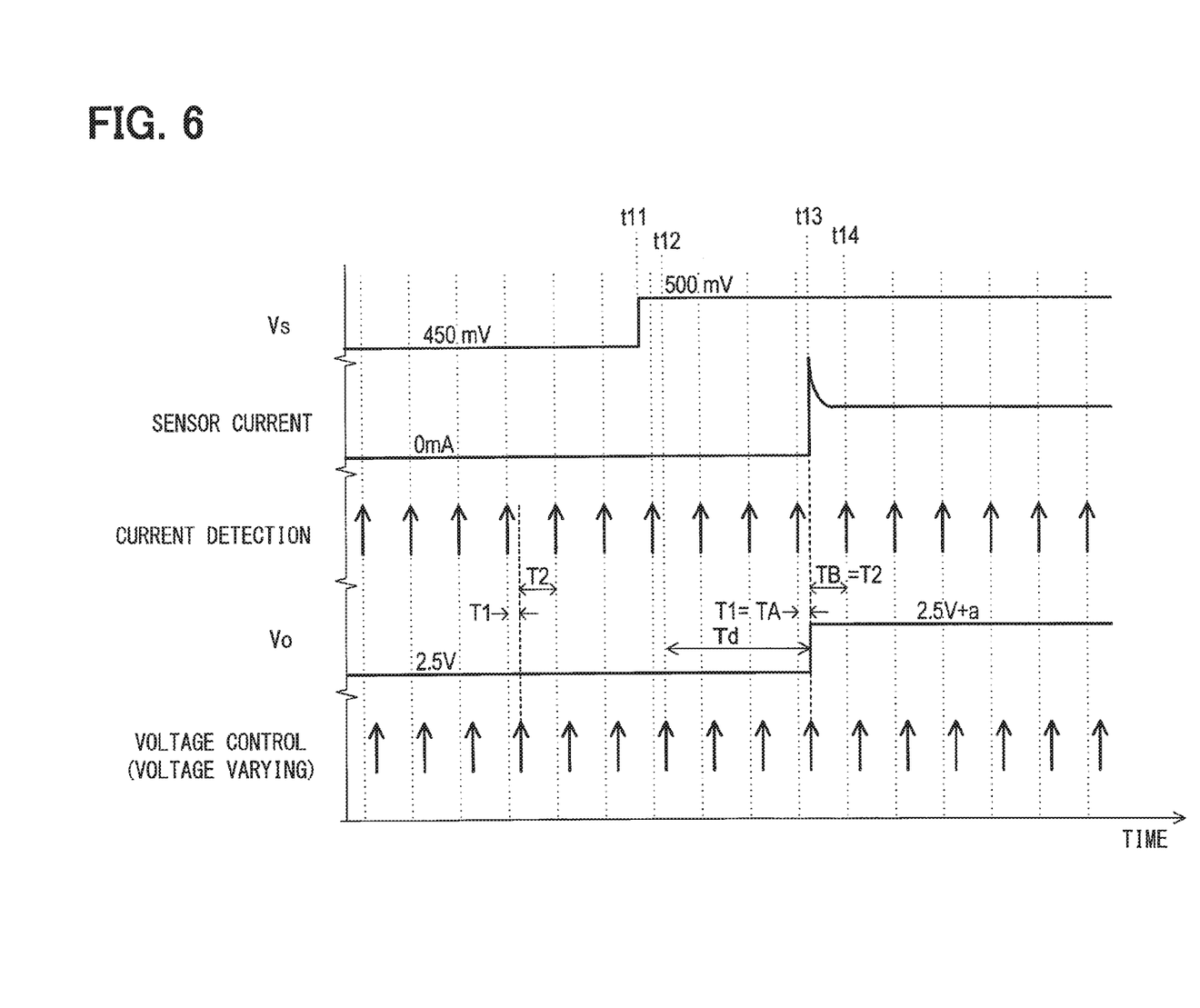
FIG. 6 is an operational diagram showing an operation of the air-fuel ratio sensor control apparatus according to the third embodiment.

The current detection part 37 commands the A/D converter 40 to convert the output voltage of the amplifier 43, that is, the current detection part 37 detects the sensor current, at time points (A/D converting time point and current detecting time point) of the fixed cycle period as indicated by an upward-directed arrow in the third stage in FIG. 6.

The voltage control part 35 controls the output voltage Vo of the D/A converter 38 at time point (voltage control time point), which is between two successive current detecting time points as indicated by an upward-directed arrow in the fifth stage in FIG. 6.

The voltage control part 35 varies the output voltage Vo of the D/A converter 38 at the voltage control time point by executing processing for varying the output voltage Vo, that is, processing for varying the digital signal applied to the D/A converter 38. As a result, the time point of voltage control is the time point, at which the voltage control part 35 varies the application voltage to the pump cell 23a, (that is, voltage varying time point).

That is, according to the ECU 21, the current detecting time point for detecting the sensor current flowing in the pump cell 23a by the current detection part 37 and the voltage varying time point for varying the application voltage to the pump cell 23a by the voltage control part 35 in accordance with the output voltage Vs of the electromotive cell 23b are shifted from each other.

As shown in FIG. 6, the time period T1, which is from the current detecting time point to the next voltage control time point, is set to be shorter than the time period T2, which is from the voltage control time point to the next current detecting time point, that is, T1<T2. That is, the time period T1 is shorter than one-half of the cycle period of current detection.

For this reason, when the output voltage Vo of the D/A converter 38 is varied at any one of the voltage control time points, a time period TA from the current detecting time point, which immediately precedes the voltage varying time point, to the voltage varying time point equals the time period T1. A time period TB from the voltage varying time point to the current detecting time point, which immediately follows the voltage varying time point, equals the time period T2. As a result, the time period TA is shorter than the time period TB. The time period TB is longer than the time period TA.

It is assumed in FIG. 6, for example, that the output voltage Vs of the electromotive cell 23b varies from the constant voltage (for example, 450 mV) in response to a variation in the air-fuel ratio at time point t11 and the voltage control part 35 acquires the voltage after the voltage variation at time point t12, which is the voltage control time point immediately following the time point t11. In this case, the voltage control part 35 acquires the output voltage Vs at a time point (hereinafter referred to as voltage acquiring time point). However, the voltage control part 35 may acquire the output voltage Vs at the other voltage acquiring time point (for example, current detecting time point), which is different from the voltage control time point.

In this case, at any one of the voltage control time points, which are after time point t12, the voltage control part 35 varies the output voltage Vo of the D/A converter 38 so that the output voltage Vs of the electromotive cell 23b restores the previous constant voltage. In this exemplary case, the voltage control part 35 varies the output voltage Vo of the D/A converter 38 at time t13, which is the voltage control time point after an elapse of a predetermined processing time period Td from time t12. With this variation of the output voltage Vo, the application voltage to the pump cell 23a varies stepwisely and the capacitive current flows in the pump cell 23a. As a result, as shown at time point t13, the capacitive current is included in the sensor current.

In case that the current detection part 37 detects the capacitive current flowing in the pump cell 23a as a part of the sensor current, the accuracy of air-fuel ratio detection is lowered. According to the ECU 21, as described above, the voltage control time point (that is, voltage varying time point) and the current detecting time point are shifted from each other. For this reason, the current detection part 37 detects the sensor current at the current detecting time point after time point t13, at which the application voltage to the pump cell 23a is varied, that is, at time t14, which is after time point t13 by the time period T2=TB. At time point t14, the capacitive current is sufficiently reduced and the sensor current is converged to a value, which indicates the actual air-fuel ratio.

[3-3. Advantage]

(3a) Similarly to the first embodiment, according to the ECU 21, the voltage varying time point of the voltage control part 35 and the current detecting time point of the current detection part 37 are shifted from each other. In case that the application voltage to the pump cell 23a is varied by the voltage control part 35, the current detection part 37 detects the current at the time point shifted from the time point of voltage variation. It is thus possible to suppress the capacitive current of the pump cell 23a from being included in the sensor current, which the current detection part 37 detects. As a result, it is possible to improve the accuracy of detecting the air-fuel ratio based on the detected current.

(3b) Similarly to the first embodiment, the current is detected at every fixed time interval and the voltage is varied at the time point, which is between the successive two of the current detecting time points. Further, the time period TA from the current detecting time point, which is immediately before the voltage varying time point, to the voltage varying time point is set to be shorter than the time period TB from the voltage varying time point to the current detecting time point, which is immediately after the voltage varying time point.

It is allowable to set that the time period TA is longer than the time period TB, that is, TA>TB, as opposed to the above-described setting TA<TB. It is however preferred to lengthen the time period TB, which is from varying the application voltage to the pump cell 23a to detecting the sensor current, by setting TA<TB. By thus lengthening the time period TB, it is easier to suppress the possibility that the capacitive current is detected as a part of the sensor current.

(3c) The current detection part 37 detects the current of the pump cell 23a as a target cell. The voltage control part 35 acquires the output voltage Vs of the electromotive cell 23b as a predetermined physical value outputted from the air-fuel ratio sensor 23 and controls the application voltage to the pump cell 23a so that the output voltage Vs attains the constant voltage. It is thus possible to use the ECU 21 for the two-cell type air-fuel ratio sensor.

4. Fourth Embodiment

[4-1. Difference from Third Embodiment]

A fourth embodiment is similar to the third embodiment in basic configuration and hence only differences from the third embodiment will be described. The same reference signs indicate the same configuration as the third embodiment.

The ECU 21 according to the fourth embodiment is different from the first embodiment in that the current detection part 37 executes detection stop processing shown in FIG. 3 at the fixed time interval in a similar manner as in the second embodiment. However, the current detection part 37 checks at 5110 in FIG. 3 whether the application voltage to the pump cell 23a is varied by the voltage control part 35. Specifically, the current detection part 37 checks whether the first voltage Vo1 of the D/A converter 38 was varied.

[4-2. Operation]

Figure 7:
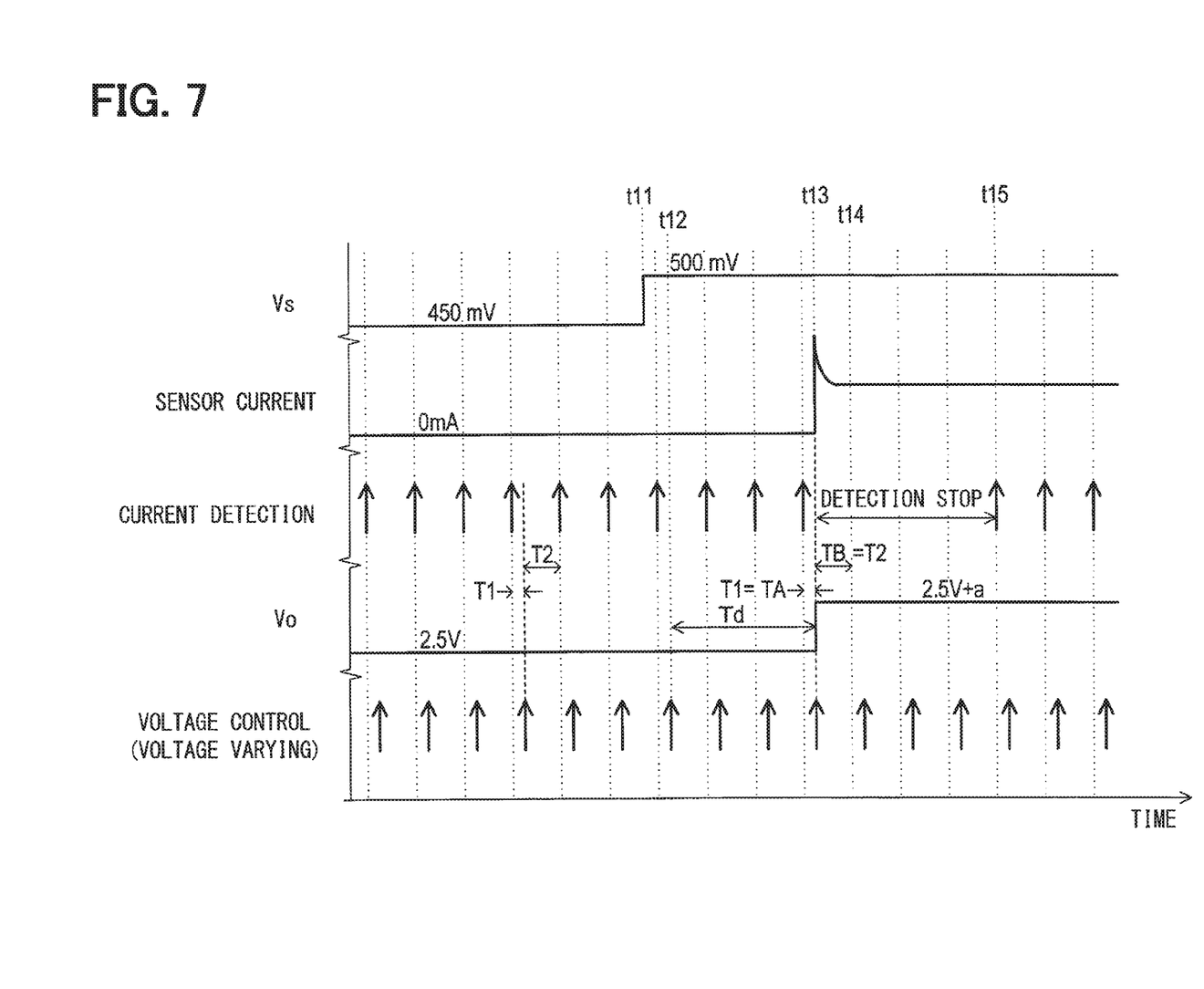
FIG. 7 is an operational diagram showing an operation of the air-fuel ratio sensor control apparatus according to the fourth embodiment.

In operation, as shown in FIG. 7, which shows a similar example of operation as FIG. 6, when the voltage control part 35 varies the output voltage Vo of the D/A converter 38 at time point t13, the current detection part 37 stops detecting the sensor current for the predetermined time period. The current detection part 37 starts again detecting the sensor current from time point t15, which is the current detecting time point after an elapse of the predetermined time period. In FIG. 7, the operation from time point t11 to time point t13 is the same as in FIG. 6. In the example shown in FIG. 7, N is assumed to be 3 similarly to the case shown in FIG. 4. That is, the current detection part 37 stops detecting the sensor current from time point t13 to the third current detecting time point and detects the sensor current again at time point t15, which is the fourth current detecting time point.

[4-3. Advantage]

The fourth embodiment provides the following advantage in addition to the similar advantages of the third embodiment. That is, when the voltage control part 35 varies the application voltage to the pump cell 23a, the current detection part 37 stops the sensor current detection for the predetermined time period. It is thus possible to more surely suppress the capacitive current, which flows in response to the variation of the applied voltage, from being detected as a part of the sensor current.

5. Other Embodiment

The present disclosure is not limited to the embodiments described above but may be implemented with the following modifications.

In the ECU 1 according to the first embodiment and the second embodiment, the second voltage Vo1 of the second D/A converter 9, that is, the voltage applied to the negative-side terminal 3n of the cell 3a by the second voltage control part 6, may be variably controlled in accordance with the sensor current. In this case, the second voltage control part 6 operates as the voltage control part. In the ECU 1 according to the first embodiment and the second embodiment, both of the first voltage Vo1 of the first A converter 8 and the second voltage Vo1 of the second D/A converter 9 may be variably controlled in accordance with the sensor current. In this case, both of the first voltage control part 5 and the second voltage control part 6 operate as the voltage control part.

What is claimed is:

1. An air-fuel ratio sensor control apparatus comprising:
    a voltage control part configured to control a voltage applied to a cell of an air-fuel ratio sensor in accordance with a predetermined physical value outputted from the air-fuel ratio sensor; and
    a current detection part configured to detect a current flowing in the cell as a physical value, which indicates the air-fuel ratio, wherein
    the voltage control part and the current detection part are configured to vary the voltage at voltage varying time points separated by a first periodic interval and detect the current at current detecting time points separated by a second periodic interval, the first periodic interval of the voltage varying time points and the second periodic interval of the current detecting time points are shifted from each other,
    the current detection part is configured to detect a current variation that occurs at a time point t1 in the cell of the air-fuel ratio sensor at a time point t2,
    the voltage control part is configured to step the voltage after a predetermined processing time period Td after the time point t2 at a time point t3 in response to the current variation in the cell of the air-fuel ratio sensor,
    the current detecting time points include time point t2,
    the voltage varying time points include time point t3, and
    the predetermined processing time period Td is longer than the second periodic interval.

2. The air-fuel ratio sensor control apparatus according to claim 1, wherein:
    each of the voltage varying time points is set to be between successive two of the current detecting time points; and
    a time period from each of the current detecting time points that are immediately before each of the voltage varying time points to each of the voltage varying time points is set to be shorter than a time period from each of the voltage varying time points to each of the current detecting time points that are immediately after the voltage varying time points.

3. The air-fuel ratio sensor control apparatus according to claim 1, wherein:
    the current detection part stops detecting the current for a predetermined time period after the voltage control part varied the voltage.

4. The air-fuel ratio sensor control apparatus according to claim 1, wherein:
    the air-fuel ratio sensor is a single cell type having a single cell, which is configured to vary the current flowing therein in accordance with the air-fuel ratio under a state that the voltage is applied thereto;
    the current detection part is configured to detect the current flowing in the single cell; and
    the voltage control part is configured to control the voltage in accordance with the current detected by the current detection part as the predetermined physical value.

5. The air-fuel ratio sensor control apparatus according to claim 1, wherein:
    the air-fuel ratio sensor is a two-cell type having a pump cell and an electromotive cell;
    the current detection part is configured to detect the current flowing in the pump cell; and
    the voltage control part is configured to acquire an output voltage of the electromotive cell as the predetermined physical value and control a voltage applied to the pump cell so that the output voltage of the electromotive cell attains a constant voltage.

6. The air-fuel ratio sensor control apparatus according to claim 3, wherein:
    the predetermined time period is set to be more than an integer times of the second periodic interval of the current detecting time points.

7. The air-fuel ratio sensor control apparatus according to claim 1, wherein:
    the voltage control part is directly connected to the current detection part.

8. The air-fuel ratio sensor control apparatus according to claim 7, wherein:
    the current detected by the current detection part is directly input into the voltage control part.

9. The air-fuel ratio sensor control apparatus according to claim 8, wherein:
   a time period between the time point t2 and the time point t3 is defined as T1;
   a time period between the time point t3 and a next current detecting time point corresponding to a time point t4 is defined as T2; and
   the time period of T1 is shorter than the time period of T2.

10. The air-fuel ratio sensor control apparatus according to claim 9, wherein:
   the time period of T1 is shorter than one-half of the second periodic interval of the current detecting time points.

* * * * *